US009144547B2

(12) United States Patent
Li et al.

(10) Patent No.: US 9,144,547 B2
(45) Date of Patent: Sep. 29, 2015

(54) ORAL DOSAGE FORM FOR CONTROLLED DRUG RELEASE

(75) Inventors: Chi Leung Li, Harlow (GB); Luigi Martini, Harlow (GB); Vincenzo Re, Harlow (GB); Helen Anne Willy, Harlow (GB)

(73) Assignee: Glaxo Group Limited, Brentford, Middlesex (GB)

( * ) Notice: Subject to any disclaimer, the term of this patent is extended or adjusted under 35 U.S.C. 154(b) by 222 days.

(21) Appl. No.: 12/966,323

(22) Filed: Dec. 13, 2010

(65) Prior Publication Data

US 2011/0135695 A1 Jun. 9, 2011

Related U.S. Application Data

(63) Continuation of application No. 10/502,376, filed as application No. PCT/GB03/00594 on Feb. 12, 2003, now abandoned.

(30) Foreign Application Priority Data

| Feb. 12, 2002 | (GB) | 0203296.9 |
| Feb. 12, 2002 | (GB) | 0203297.7 |
| Feb. 12, 2002 | (GB) | 0203298.5 |

(51) Int. Cl.
A61K 9/20 (2006.01)
A61K 9/24 (2006.01)
A61K 9/28 (2006.01)

(52) U.S. Cl.
CPC .................................. *A61K 9/2072* (2013.01)

(58) Field of Classification Search
None
See application file for complete search history.

(56) References Cited

U.S. PATENT DOCUMENTS

| 4,449,983 A * | 5/1984 | Cortese et al. ............ 604/892.1 |
| 4,556,552 A | 12/1985 | Porter et al. ................. 424/32 |
| 4,704,295 A | 11/1987 | Porter et al. .................. 427/3 |
| 4,769,027 A | 9/1988 | Baker et al. ................ 424/493 |
| 4,775,536 A | 10/1988 | Patell ........................ 424/471 |
| 4,816,262 A | 3/1989 | McMullen ................... 424/467 |
| 4,983,401 A | 1/1991 | Eichel et al. ................ 424/473 |
| 5,004,614 A * | 4/1991 | Staniforth ................... 424/466 |
| 5,326,571 A | 7/1994 | Wright et al. ................ 424/473 |
| 5,342,627 A | 8/1994 | Chopra et al. ............... 424/473 |
| 5,366,738 A | 11/1994 | Rork et al. ................... 424/473 |
| 5,431,921 A * | 7/1995 | Thombre .................... 424/424 |
| 5,500,227 A | 3/1996 | Oshlack et al. ............... 424/476 |
| 5,520,931 A | 5/1996 | Persson et al. ............... 424/473 |
| 5,681,584 A * | 10/1997 | Savastano et al. ............ 424/473 |
| 5,879,706 A | 3/1999 | Carter et al. |
| 5,955,103 A | 9/1999 | Jao et al. .................... 424/457 |
| 6,039,976 A | 3/2000 | Mehra et al. ................. 424/480 |
| 6,068,859 A | 5/2000 | Curatolo et al. |
| 6,099,859 A | 8/2000 | Cheng et al. |
| 6,264,985 B1 | 7/2001 | Cremer ...................... 424/473 |
| 6,287,599 B1 | 9/2001 | Burnside et al. ............. 424/468 |
| 6,387,403 B1 | 5/2002 | Seroff et al. ................. 424/473 |
| 6,387,404 B2 | 5/2002 | Oshlack et al. .............. 424/480 |
| 6,475,521 B1 * | 11/2002 | Timmins et al. ............. 424/469 |
| 6,569,463 B2 | 5/2003 | Patel et al. .................. 424/497 |
| 6,667,060 B1 | 12/2003 | Vandecruys et al. ......... 424/488 |
| 6,787,156 B1 | 9/2004 | Bar-Shalom ................. 424/480 |
| 8,637,512 B2 | 1/2014 | Buxton et al. |
| 2002/0012675 A1 | 1/2002 | Jain et al. .................... 424/400 |
| 2002/0051814 A1 | 5/2002 | Chen ......................... 424/451 |
| 2002/0099361 A1 * | 7/2002 | Faour ....................... 604/892.1 |
| 2002/0127263 A1 * | 9/2002 | Carlyle et al. ............... 424/423 |
| 2002/0136744 A1 | 9/2002 | McGlynn et al. ............ 424/400 |
| 2003/0056896 A1 | 3/2003 | Jao et al. ..................... 156/327 |
| 2003/0203027 A1 | 10/2003 | Verreck et al. .............. 424/471 |
| 2004/0018327 A1 | 1/2004 | Wynn et al. ................. 428/35.7 |
| 2004/0062806 A1 | 4/2004 | Martini et al. ............... 424/473 |
| 2004/0146556 A1 | 7/2004 | Noack et al. ................ 424/468 |
| 2004/0192690 A1 | 9/2004 | Buxton et al. ............... 514/242 |
| 2004/0219209 A1 | 11/2004 | Chen et al. .................. 424/468 |

(Continued)

FOREIGN PATENT DOCUMENTS

| EP | 166319 B1 | 3/1993 |
| EP | 631775 B1 | 8/1999 |

(Continued)

OTHER PUBLICATIONS

"Practical Course in Film Coating of Pharmaceutical Dosage Forms with EUDRAGIT®". http://www.roehm.de/en/pharmapolymers/content=/en/pharmapolymers/service/literature/practical_course Mar. 2000.

(Continued)

*Primary Examiner* — Susan Tran

(74) *Attorney, Agent, or Firm* — Kathryn A. Lutomski; John Lemanowicz; William R. Majarian

(57) ABSTRACT

An oral dosage form comprising, (i) an erodable core, which core comprises a pharmaceutically active weak base or a pharmaceutically acceptable salt or solvate thereof; and (ii) an erodable coating surrounding said core, which coating comprises one or more openings extending substantially completely through said coating but not penetrating said core and communicating from the environment of use to said core;

characterized in that release of the pharmaceutically active weak base or a pharmaceutically acceptable salt or solvate thereof from the dosage form occurs through the said opening(s) by the erosion of said erodable core and through erosion of said erodable coating under pre-determined pH conditions; a process for preparing such a dosage form and the use of such a dosage form in medicine.

8 Claims, 1 Drawing Sheet

(56) References Cited

U.S. PATENT DOCUMENTS

| | | |
|---|---|---|
| 2004/0245675 A1 | 12/2004 | Clarke et al. .................. 264/275 |
| 2005/0163845 A1 | 7/2005 | Conte et al. ................... 424/472 |
| 2007/0134326 A1 | 6/2007 | Hoke et al. .................... 424/468 |
| 2007/0141146 A1 | 6/2007 | Re et al. ......................... 424/468 |
| 2007/0275054 A1 | 11/2007 | Lewis et al. ................... 424/452 |
| 2007/0275063 A1 | 11/2007 | Benincosa et al. ............. 424/468 |
| 2007/0281023 A1 | 12/2007 | Glinecke et al. ............... 424/472 |
| 2008/0014266 A1 | 1/2008 | Lewis et al. ................... 424/465 |
| 2008/0124393 A1 | 5/2008 | Swanson et al. ............... 424/465 |
| 2008/0139624 A1 | 6/2008 | Re ................................. 514/342 |
| 2008/0166408 A1 | 7/2008 | Heafield et al. ................ 424/472 |
| 2008/0206336 A1 | 8/2008 | Coles et al. .................... 424/474 |

FOREIGN PATENT DOCUMENTS

| | | |
|---|---|---|
| GB | 2 150 830 | 7/1985 |
| WO | WO 90/01925 | 3/1990 |
| WO | WO 93/09785 A1 | 5/1993 |
| WO | WO 95/22962 A1 | 8/1995 |
| WO | WO 9522962 A1 * | 8/1995 |
| WO | WO 95/29665 A1 | 11/1995 |
| WO | WO 96/01612 | 1/1996 |
| WO | WO 96/17611 | 6/1996 |
| WO | WO 97/14415 | 4/1997 |
| WO | WO 98/47491 | 10/1998 |
| WO | WO 99/11211 A1 | 3/1999 |
| WO | WO 99/26606 A2 | 6/1999 |
| WO | WO 99/48481 | 9/1999 |
| WO | WO 99/51208 A1 | 10/1999 |
| WO | WO 2001/05430 A1 | 1/2001 |
| WO | WO 01/47498 A2 | 7/2001 |
| WO | WO 02/17918 A2 | 3/2002 |
| WO | WO 02/34240 A2 | 5/2002 |
| WO | WO 02/38131 | 5/2002 |
| WO | WO 02/055009 A1 | 7/2002 |
| WO | WO 03/024430 A1 | 3/2003 |
| WO | WO 03/026625 A1 | 4/2003 |
| WO | WO 03/026626 A2 | 4/2003 |
| WO | WO 03/053400 A1 | 7/2003 |
| WO | WO 03/063823 A2 | 8/2003 |
| WO | WO 03/063868 A1 | 8/2003 |
| WO | WO 03/068195 A1 | 8/2003 |
| WO | WO 03/070225 A1 | 8/2003 |
| WO | WO 03/075893 A1 | 9/2003 |
| WO | WO 03/075894 A1 | 9/2003 |
| WO | WO 03/075897 | 9/2003 |
| WO | WO 03/082207 A2 | 10/2003 |
| WO | WO 03/086364 A1 | 10/2003 |
| WO | WO 03/090732 A1 | 11/2003 |
| WO | WO 03/092649 A2 | 11/2003 |
| WO | WO 03/092660 A1 | 11/2003 |
| WO | WO 03/094888 A1 | 11/2003 |
| WO | WO 03/096968 A2 | 11/2003 |
| WO | WO 03/101384 A2 | 12/2003 |
| WO | WO 03/103637 A2 | 12/2003 |
| WO | WO 03/104192 A2 | 12/2003 |
| WO | WO 2005/013935 | 2/2005 |
| WO | WO 2005/013956 | 2/2005 |

OTHER PUBLICATIONS

Datasheet for Registration of EUDRAGIT® Acrylic Polymers. International Availability and Acceptance for Use in the Manufacture of Pharmaceutical Dosage Forms. (1999).

ACRYL-EZE®, Product Information (2008), www.colorcon.com/products/coatings/enteric-delayed-release/acryt-eze.

Rohm Pharma polymers, pp. 1-4 (2001).

U.S. Appl. No. 10/726,752: Office Action dated May 29, 2007.

U.S. Appl. No. 10/726,752: Sep. 17, 2007 Applicant Response to May 29, 2007 Office Action.

U.S. Appl. No. 10/726,752: Final Office Action dated Nov. 28, 2007.

U.S. Appl. No. 10/726,752: Apr. 10, 2008 Applicant Response to Nov. 28, 2007 Final Office Action.

U.S. Appl. No. 10/726,752: Office Action dated Feb. 5, 2009.

U.S. Appl. No. 10/726,752: Aug. 4, 2009 Applicant Response to Feb. 5, 2009 Office Action.

U.S. Appl. No. 10/726,752: Final Office Action dated Nov. 25, 2009.

U.S. Appl. No. 10/726,752: Mar. 12, 2010 Applicant Response to Nov. 25, 2009 Final Office Action.

U.S. Appl. No. 10/726,752: Office Action dated Jun. 9, 2011.

U.S. Appl. No. 10/726,752: Sep. 7, 2011 Applicant Response to Jun. 9, 2011 Office Action.

U.S. Appl. No. 10/726,752: Final Office Action dated Oct. 27, 2011.

U.S. Appl. No. 10/726,752: Jan. 25, 2012 Applicant Response to Oct. 27, 2011 Final Office Action.

* cited by examiner

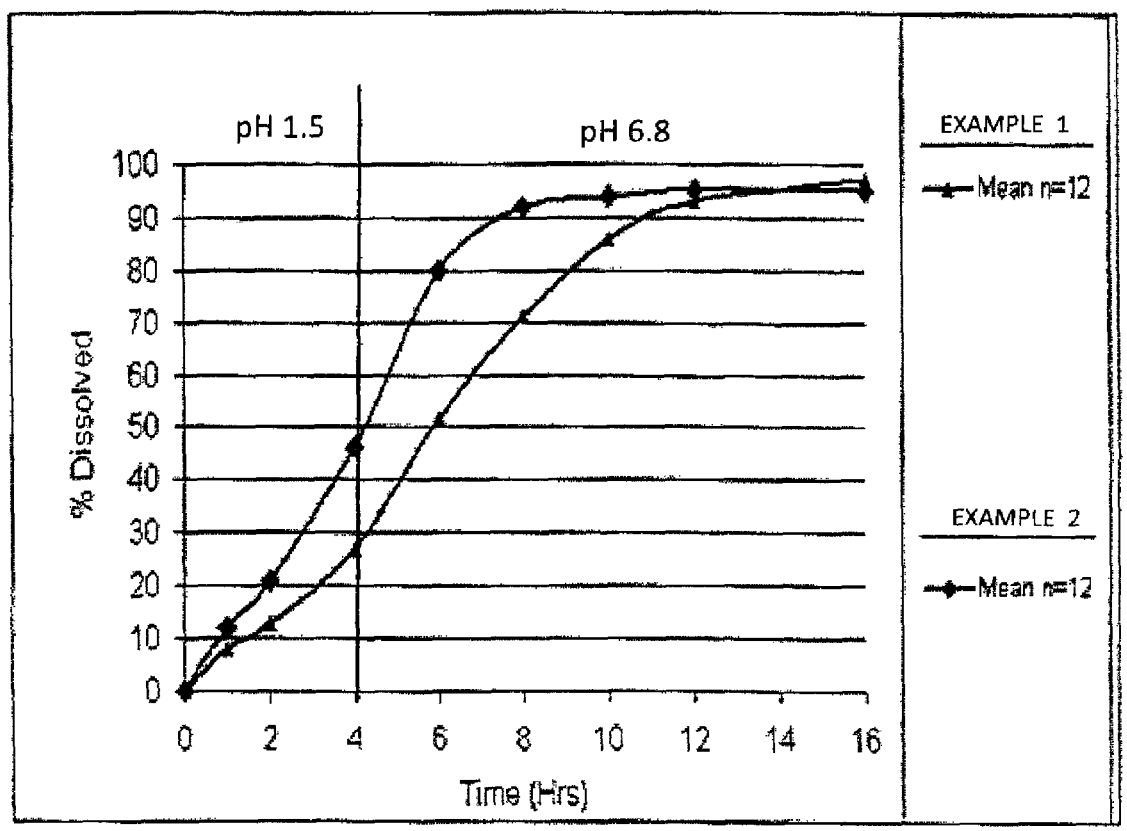

ORAL DOSAGE FORM FOR CONTROLLED DRUG RELEASE

This application is a continuation of application Ser. No. 10/502,376, filed 4 Apr. 2005, now abandoned which is a 371 of International Application No. PCT/GB03/00594, filed 12 Feb. 2003, which claims priority to Great Britain Application Nos. 0203296.9, filed 12 Feb. 2002, 0203297.7, filed 12 Feb. 2002, and 0203298.5, filed 12 Feb. 2002.

FIELD OF THE INVENTION

The invention relates to an oral dosage form which provides controlled release of an active pharmaceutical agent in different body environments, to a process for preparing such a dosage form and to the use of such a dosage form in medicine.

BACKGROUND TO THE INVENTION

The use of a coating to control the rate of release of an active agent has received considerable attention and many different devices have been developed for such a purpose. For example, International Patent Application, Publication Number WO 01/05430 describes a drug delivery device that enables the delivery of drug substances which exhibit pH dependent solubility, in particular compounds that are more soluble at low pH levels (less than pH 2) than at near neutral levels (greater than about pH 5). Such delivery devices are characterised by the presence of a coating that is impermeable and insoluble in the fluid of the environment of use.

International patent application, Publication Number WO 95/30422 describes a series of controlled-release dosage forms of azithromycin. In particular, there is described a series of dosage forms that reduce the exposure of the upper GI tract (e.g. the stomach) to high concentrations of azithromycin, by the use of a pH dependent coating. Such dosage forms do not feature openings through which release of the drug substance may occur.

U.S. Pat. No. 6,099,859 describes a controlled release tablet for the delivery of an antihyperglycemic drug, which comprises an osmotically active drug-containing core and a semipermeable membrane, wherein the semipermeable membrane is permeable to the passage of water and biological fluids and is impermeable to the passage of the drug substance. The semipermeable membrane contains at least one passageway for the release of the antihyperglycemic drug.

Additional devices that utilise a coating to control the rate of release of an active agent are discussed in U.S. Pat. No. 5,004,614. This patent describes a tablet core provided with an outer coating that is substantially impermeable to environmental fluid. The said outer coating may be prepared from materials that are either insoluble or soluble in the environmental fluids. Where a soluble material is used, the coating is of sufficient thickness that the core is not exposed to environmental fluid before the desired duration of the controlled release of the active agent has passed. Through this impermeable outer coating, one or more opening(s) has been created, so as to provide environmental fluids with an access route to the core. Therefore, upon ingestion of the coated tablet, gastro-intestinal fluid can enter the opening(s) and contact or penetrate the core, to release the active agent. The result is that the active agent is released in a controlled manner out of the opening(s) only. The preferred geometry is such that there is a circular hole on the top and bottom face of the coated tablet. The opening(s) in question have an area from about 10 to 60 percent of the face area of the coated tablet. The rate of drug release is found to be directly related to the diameter of the opening(s) and to the solubility of the matrix core and active agent, allowing the possibility for a variety of drug release profiles be it zero or first order release.

This invention is based on the finding that the substantially impermeable coatings of U.S. Pat. No. 5,004,614 are not suitable for the controlled release of all active agents, especially pharmaceutically active weak bases or pharmaceutically acceptable salts and solvates thereof. Such active agents exhibit a marked pH dependent solubility, i.e. they are more soluble at around pH 2, associated with regions found in the stomach, compared to their solubility in the generally neutral conditions of the small intestine, around pH 7.

We have found that for administration of a pharmaceutically active weak base or a pharmaceutically acceptable salt or solvate thereof, where it is desirable that release of the active compound takes place in more than one pH environment, it is beneficial for the coating to be erodable or soluble in a pH dependent manner.

SUMMARY OF THE INVENTION

Accordingly, in its broadest aspect the present invention provides an oral dosage form comprising an erodable core which contains a pharmaceutically active weak base or a pharmaceutically acceptable salt or solvate thereof, the core having a coating with one or more openings leading to the core, characterised in that the coating is erodable under predetermined pH conditions.

The present invention further provides an oral dosage form comprising,
(i) an erodable core, which core comprises a pharmaceutically active weak base or a pharmaceutically acceptable salt or solvate thereof; and
(ii) an erodable coating around said core, which coating comprises one or more openings extending substantially completely through said coating but not penetrating said core and communicating from the environment of use to said core;

characterised in that release of the pharmaceutically active weak base or a pharmaceutically acceptable salt or solvate thereof from the erodable core occurs substantially through the said opening(s) and through erosion of said erodable coating under pre-determined pH conditions.

For the avoidance of doubt, as used herein the term "weak base" shall mean any base the conjugate acid of which has a pKa of less than 11.5; in accordance with *The Pharmaceutical Handbook*, 19th Edition, 1980. The term "pharmaceutically acceptable weak base" shall be interpreted accordingly. Suitably, pharmaceutically acceptable weak bases or pharmaceutically acceptable salts or solvates thereof for use in the present invention exhibit a marked pH dependent solubility. Preferably, pharmaceutically acceptable weak bases or pharmaceutically acceptable salts or solvates thereof for use in the present invention are more soluble in the pH range from 1 to 3 compared to their solubility in the pH range from 4.5 to 8. Preferred pharmaceutically acceptable weak bases or pharmaceutically acceptable salts or solvates thereof for use in the present invention are more soluble in the acidic conditions found in the mammalian stomach than in the near neutral conditions of the mammalian intestines.

Suitable pharmaceutically active weak bases for use in the present invention include—1-(3-Chlorophenyl)-2-[(1,1-dimethylethyl)amino]-1-propanone ("bupropion"), 1,2,3,9-Tetrahydro-9-methyl-3-[(2-methyl-1H-imidazol-1-yl)methyl]-4H-carbazol-4-one ("ondansetron"), (3S-trans)-3-[(1,3-Benzodioxol-5-yloxy)methyl]-4-(4-fluorophenyl)piperidine ("paroxetine"), α¹-[[1,1-Dimethylethyl)amino]methyl]-4-hydroxy-1,3-benzenedimethanol ("salbutamol") and pharmaceutically acceptable salts and/or solvates thereof.

European Patent Application, Publication Number 0 306 228 A1 relates to certain thiazolidinedione derivatives disclosed as having antihyperglycaemic and hypolipidaemic activity. One particular thiazolidinedione disclosed in EP 0 306 228 A1 is 5-[4-[2-(N-methyl-N-(2-pyridyl)amino) ethoxy]benzyl]thiazolidine-2,4-dione (hereinafter 'Compound A'). International Patent Application, Publication Number WO 94/05659 discloses certain salts of Compound A including the maleate salt at Example 1 thereof.

Compound A and pharmaceutically acceptable salts or solvates thereof have useful pharmaceutical properties. In particular Compound A or a salt or solvate thereof is indicated to be useful for the treatment and/or prophylaxis of diabetes mellitus, conditions associated with diabetes mellitus and certain complications thereof.

A preferred pharmaceutically active weak base for use in the present invention is Compound A or a pharmaceutically acceptable salt or solvate thereof. A particularly preferred pharmaceutically active weak base for use in the present invention is the maleate salt of Compound A.

A further preferred pharmaceutically active weak base for use in the present invention is valaciclovir or a pharmaceutically acceptable salt thereof. Valaciclovir is the L-valine ester of acyclovir and is named 2-[(2-amino-1,6-dihydro-6-oxo-9H-purin-9-yl)methoxy]ethyl L-valinate. A preferred salt of this compound is the hydrochloride salt, known as valaciclovir hydrochloride. Valaciclovir and the hydrochloride salt thereof are disclosed in U.S. Pat. No. 4,957,924 (see particularly Example IB), European Patent Number EP 0 308 065 B1 (see particularly Example IB), and L. M. Beauchamp et al, *Antiviral Chemistry and Chemotherapy*, 3(3), 157-164 (1992) (see particularly page 162 column 1), all of which are incorporated herein by reference as though fully set forth. A preferred anhydrous crystalline form of valaciclovir hydrochloride is disclosed in International Patent Application, Publication Number WO 96/22291 (incorporated herein by reference as though fully set forth); this anhydrous crystalline form can for example be defined by having substantially the X-ray powder diffraction pattern of one or more of FIGS. 1 to 3 of WO 96/22291. Some syntheses of valaciclovir and its hydrochloride salt are given in WO 96/22291, e.g. see Examples 1A/B and 2A/B and pages 4-7 therein.

Valaciclovir or a salt thereof can be used in the treatment and/or suppression of a viral infection in a mammal such as a human, particularly a viral infection caused by the herpes group of viruses, e.g. herpes zoster and/or herpes simplex virus types 1 or 2. The following dosage regimes, wherein the doses are calculated as the valaciclovir free base, are given for guidance:
(a) treatment of episodes of herpes simplex virus types 1 and 2 infection:—total daily dose of about 1 or 2 g administered at 500 mg twice a day or 1 g twice a day for 5 to 10 days;
(b) suppression of recurrences of herpes simplex virus types 1 and 2 infections (e.g. genital herpes):—total daily dose about 250 to 1 g (e.g. 500 mg twice a day) for about one month to ten years, depending on the patient. As disclosed in WO 97/25989 (incorporated herein by reference), valaciclovir or a salt thereof can also be used in the suppression of recurrent genital herpes in a human at a once daily dose of from about 200 mg to about 1000 mg (e.g. 250 mg, 500 mg or 1000 mg) valaciclovir or a salt thereof (calculated as the free base) for an effective treatment period e.g. for ca. 2 months up to ca. 10 years.
(c) treatment of varicella zoster virus infections (herpes zoster, e.g. shingles):—total daily dose about 3 g administered at 1 g three times a day for 7 days;
(d) suppression of cytomegalovirus infections:—total daily dose about 8 g administered at 2 g 4 times a day; for transplant patients this daily dose is administered for three to six months for the period at risk; and for HIV positive patients a daily dose is administered as usually indicated for improving quality of life, for example for two years or more.

Suitably, the pharmaceutically acceptable weak base is selected from the group consisting of 1-(3-Chlorophenyl)-2-[(1,1-dimethylethyl)amino]-1-propanone ("bupropion"), 1,2,3,9-Tetrahydro-9-methyl-3-[(2-methyl-1H-imidazol-1-yl)methyl]-4H-carbazol-4-one ("ondansetron") and (3S-trans)-3-[(1,3-Benzodioxol-5-yloxy)methyl]-4-(4-fluorophenyl)piperidine ("paroxetine"), 2-[(2-amino-1,6-dihydro-6-oxo-9H-purin-9-yl)methoxy]ethyl L-valinate ("valaciclovir"), Compound A and pharmaceutically acceptable salts and/or solvates thereof (hereafter "the Primary Compounds of the invention"). Suitably, the pharmaceutically acceptable weak base is 1-(3-Chlorophenyl)-2-[(1,1-dimethylethyl)amino]-1-propanone ("bupropion") or a pharmaceutically acceptable salt or solvate thereof. Suitably, the pharmaceutically acceptable weak base is 1,2,3,9-Tetrahydro-9-methyl-3-[(2-methyl-1H-imidazol-1-yl)methyl]-4H-carbazol-4-one ("ondansetron") or a pharmaceutically acceptable salt or solvate thereof. Suitably, the pharmaceutically acceptable weak base is (3 S-trans)-3-[(1,3-Benzodioxol-5-yloxy)methyl]-4-(4-fluorophenyl)piperidine ("paroxetine") or a pharmaceutically acceptable salt or solvate thereof. More suitably, the pharmaceutically acceptable weak base is 2-[(2-amino-1,6-dihydro-6-oxo-9H-purin-9-yl)methoxy]ethyl L-valinate ("valaciclovir"). Most suitably, the pharmaceutically acceptable weak base is Compound A or a pharmaceutically acceptable salt or solvate thereof.

BRIEF DESCRIPTION OF THE DRAWINGS

FIG. 1 is a graph of dissolution against time for two formulations of oral dosage form in accordance with this invention.

DETAILED DESCRIPTION OF THE INVENTION

Typical pharmaceutically active weak bases for use in the present invention are the Primary Compounds of the invention, in particular Compound A or a pharmaceutically acceptable salt or solvate thereof. Such compounds and pharmaceutically acceptable salts thereof exhibit a marked pH dependent solubility, i.e. they are more soluble at around pH 2, associated with regions found in the stomach, compared to their solubility in the generally neutral conditions of the small intestine, around pH 7.

The Primary Compounds of the invention and pharmaceutically acceptable salts and solvates thereof have useful pharmaceutical properties which are well documented (e.g. the British and US Pharmacopoeias, Remington's Pharmaceutical Sciences (Mack Publishing Co.), Martindale The Extra Pharmacopoeia (London, The Pharmaceutical Press)).

The oral dosage form of this invention may be also be used to administer other pharmaceutically active weak bases with similar dissolution properties to the Primary Compounds of the invention, to treat disorders for which the weak base is known to be indicated.

The above reference to the coating being erodable includes the situation where the coating disintegrates partially or wholly, or dissolves, or becomes porous, on contact with an environmental fluid so as to allow the fluid to contact the core. Suitably the coating disintegrates partially. Suitably the coating disintegrates wholly. Suitably the coating dissolves. Suitably the coating becomes porous.

Similarly the references to the core being erodable includes the situation where core disintegrates partially or wholly, or dissolves, or becomes porous, on contact with an environmental fluid so as to allow the fluid to contact the active agent. Suitably the core disintegrates partially. Suitably the core disintegrates wholly. Suitably the core dissolves. Suitably the core becomes porous.

While this invention provides that erosion of the coating is pH-dependent, the core may release the pharmaceutically active weak base or a pharmaceutically acceptable salt or solvate thereof by eroding in a non-pH dependent manner. However to suit a specific demand, the core may be a material which allows pH dependent erosion or disintegration of the core to release the pharmaceutically active weak base or a pharmaceutically acceptable salt or solvate thereof from its matrix.

Most suitably, although the pharmaceutically active weak base or a pharmaceutically acceptable salt or solvate thereof is more soluble in the stomach than the intestines, the core is formulated so as to be erodable to substantially the same extent under both conditions.

So that the opening(s) in the coating retains its integrity and control of release rate, it is desirable that the pH dependent erosion of the coating has a defined threshold, i.e. the coating does not substantially erode except in the intestines. Thus, it is envisaged that erosion of the coating has a defined, pre-determined pH threshold at which it dissolves. Preferably, the coating erodes at pH>4.5. More preferably, the coating erodes in the pH range from 4.5 to 8. Most preferably, the coating erodes in the pH range 5 to 7.

The present invention finds particular use in the situation where the coating erodes in the pH conditions of the intestines. Accordingly, the present invention also provides an oral dosage form comprising an erodable core which contains a pharmaceutically active weak base or a pharmaceutically acceptable salt thereof, the core having a coating with one or more openings leading to the core, characterised in that the coating is erodable under the pH conditions prevailing in a mammalian intestine.

It will be appreciated that the use of a coating that erodes at pH>4.5 will restrict the amount of drug released into the acidic conditions associated with the stomach, since release is at low pH levels is substantially limited to diffusion of the active agent through the opening(s) in the erodable coating. Thus, the present invention is indicated to address the problem of "dose dumping" in the stomach for compounds that are more soluble in the pH range from 1 to 3 than in the pH range from 4.5 to 8. As the dosage form leaves a low pH environment and then encounters a higher environmental pH, e.g. moves from the stomach into the intestine, the coating will start to dissolve and erode away to expose all of the tablet core. During coat erosion, the available surface area to release drug is increased. The decrease in drug solubility and therefore rate of drug adsorption in the intestine can be compensated for by the increase in the surface area due to all the faces of the tablet core being exposed to erosion. The result is a more balanced drug release profile in both environments.

In applying the concepts of this invention, the pharmaceutically active weak base or a pharmaceutically acceptable salt or solvate thereof may be incorporated into a conventional oral tablet or controlled release matrix (including both swellable and non-swellable systems). The matrix is formed into cores which are then coated with a material with pH-dependent erodability, for example a coating soluble at pH>4.5, such as a polymethacrylate copolymer. One or more openings may then be drilled through the coatings using conventional techniques as disclosed in U.S. Pat. No. 5,004,614.

According to a further aspect of the present invention, there is provided a process for the preparation of an oral dosage form according to the present invention, which process comprises:

(a) preparing an erodable tablet core;
(b) coating the core with a material with pH-dependent erodability; and
(c) creating one or more openings in the coating, said opening(s) extending substantially completely through said coating but not penetrating said core and communicating from the environment of use to said core.

The core may be prepared by compressing suitable ingredients to form a compacted mass which comprises the core of the dosage form (also referred to herein as "tablet core"). This may be prepared using conventional tablet excipients and formulation compression methods. Thus, the core typically comprises the active agent or agents along with excipients that impart satisfactory processing and compression characteristics such as diluents, binders and lubricants. Additional excipients that may form part of the core of the device include disintegrants, flavourants, colorants, release modifying agents and/or solubilising agents such as surfactants, pH modifiers and complexation vehicles.

Suitable materials for the core include erodable polymethylmethacrylate resins such as the Eudragit™ series, for example Eudragit™ L30D, saccharoses, for example lactose and maltose, and cellulose esters, for example methylcellulose, hydroxypropylmethylcellulose (HPMC) and hydroxypropylcellulose. Suitably, the core is predominantly hydroxypropylmethylcellulose and lactose. More suitably, the core consists essentially of hydroxypropylmethylcellulose, lactose, colloidal silicon dioxide and magnesium stearate.

Typically the active agent and excipients are thoroughly mixed prior to compression into a solid core. The core of the device may be formed by wet granulation methods, dry granulation methods or by direct compression. The core may be produced according to any desired pre-selected shape such as bi-convex, hemi-spherical, near hemi-spherical, round, oval, generally ellipsoidal, oblong, generally cylindrical or polyhedral, e.g. a triangular prism shape. The term "near hemi-spherical" is intended to be construed in the manner described in U.S. Pat. No. 5,004,614. Suitably the core is formulated into a bi-convex shape, e.g. having two domed opposite surfaces. In addition, the core may be produced in a multi-layered (e.g. bi- or tri-layered) form.

The quantity of the pharmaceutically active weak base or a pharmaceutically acceptable salt or solvate thereof present within the core is a matter to be determined based upon typical pharmaceutical considerations, e.g. known dosages for the pharmaceutically active weak base or a pharmaceutically acceptable salt or solvate thereof, and is not limited by the process of this invention.

In particular, where Compound A or a pharmaceutically salt or solvate thereof is used in accordance with the present invention, a suitable dosage range is 2 to 12 mg. Thus, suitable dosage forms comprise 2, 3, 4, 5, 6, 7, 8, 9, 10, 11 or 12 mg of Compound A or a pharmaceutically acceptable salt or solvate thereof.

Particular dosage forms comprise 2 to 4 mg of Compound A or a pharmaceutically acceptable salt or solvate thereof.

Particular dosage forms comprise 4 to 8 mg of Compound A or a pharmaceutically acceptable salt or solvate thereof.

Particular dosage forms comprise 8 to 12 mg of Compound A or a pharmaceutically acceptable salt or solvate thereof.

One dosage form comprises 2 mg of Compound A or a pharmaceutically acceptable salt or solvate thereof.

Preferred dosage forms comprise 4 mg of Compound A or a pharmaceutically acceptable salt or solvate thereof.

Preferred dosage forms comprise 8 mg of Compound A or a pharmaceutically acceptable salt or solvate thereof.

The core may be coated with a suitable pH dependent erodable material by any pharmaceutically acceptable coating method. Examples include coating methods disclosed in U.S. Pat. No. 5,004,614 and film coating, sugar coating, spray coating, dip coating, compression coating, electrostatic coating. Typical methods include spraying the coating onto the tablet core in a rotating pan coater or in a fluidised bed coater until the desired coating thickness is achieved. Suitably the coating is provided to add about 4 to 8 mg/cm$^2$ or 5-7 mg/cm$^2$ of dry polymer around the tablet surface area. Typically this results in an increase in weight (relative to the core) of from 3-10% or 5-10% by weight. Suitably, the coating has a thickness in the range 0.05 to 0.5 mm.

Materials and their blends suitable for use as a pH-dependent erodable coating material in this invention include various polymethacrylate polymers, coprocessed polyvinylacetate phthalate, cellulose acetate trimellitate, cellulose acetate phthalate, shellac, hydroxyropylmethylcellulose phthalate polymers and their copolymers.

The coating material is suitably selected so that it is insoluble in stomach acid i.e. at pH 1.5-2, and is soluble or erodable in the small intestine i.e. at around pH 5.5 or in the large intestine i.e. at around pH 7. To achieve this, typically the material of the coating is erodable at pH of 4.5 or above.

Suitably, the coating material is selected from:
cellulose acetate trimellitate (CAT) dissolving @ pH 4.8,
polyvinyl acetate phthalate dissolving @ pH 5.0,
hydroxypropylmethylcellulose phthalate 50 dissolving @ pH 5.2,
hydroxpropylnethylcellulose phthalate 55 dissolving @ pH 5.4,
Acryl-eze™ dissolving @ pH 5.5,
Aquateric™ dissolving @ pH 5.8,
cellulose acetate phthalate dissolving @ pH 6.0,
Eudragit™ L30 D dissolving @ pH 5.5,
Eudragit™ L dissolving @ pH 6.0,
Eudragit™ S dissolving @ pH 6.8, and
shellac dissolving @ pH 7.2.

When necessary, the erodable coating may be modified by addition of plasticisers or anti-tack agents. Suitable materials for this purpose include waxy materials such as glycerides, for example glyceryl monostearate.

Typical sizes for the opening(s), when circular, to be formed in the coating are in the range 0.5 mm-8 mm of diameter, such as 1, 2, 4 or 4 mms in diameter, depending on the overall size of the tablet and the desired rate of release. The opening(s) may have any convenient geometrical shape, but a rounded shape, e.g. substantially circular or elliptical, is generally preferred. More elaborate shapes, such as text characters or graphics, may also be formed, provided that the release rate can be made uniform in individual dosage forms. Typical sizes of non-circular openings are equivalent in area to the above mentioned sizes for circular openings, thus in the range of from about 0.19 to about 50.3 mm$^2$.

For the purposes of the present invention, the term "opening" is synonymous with hole, aperture, orifice, passageway, outlet etc.

The opening(s) may be formed by methods disclosed in U.S. Pat. No. 5,004,614. Typically opening(s) may be formed by drilling, for example using mechanical drill bits or laser beams, or by punches that remove the cut area. The formation of the opening(s) may by default remove a small portion of the exposed core. It is also possible to purposely form a cavity below the aperture as a release rate controlling device, the cavity exposing a greater initial surface area of core than a flat surface. Suitably, the opening(s) extend through the entire erodable coating such that there is immediate exposure of the core to the environmental fluid when the device is placed in the desired environment of use.

Also it is possible to form the opening(s) in situ when the dosage form is administered, by forming a coating containing pore-forming agents i.e. material that will dissolve in the stomach to create pores in the coating. Accordingly, there is also provided an oral dosage form comprising, (i) an erodable core, which core comprises a pharmaceutically active weak base or a pharmaceutically acceptable salt or solvate thereof; and (ii) an erodable coating surrounding said core, which coating comprises a pore forming agent that is erodable in the pH range from 1 to 3 to form one or more openings extending substantially completely through said coating but not penetrating said core and communicating from the environment of use to said core;

characterised in that release of the pharmaceutically active weak base or a pharmaceutically acceptable salt or solvate thereof from the dosage form occurs through the said opening(s) by the erosion of said erodable core and through erosion of said erodable coating under pre-determined pH conditions.

In U.S. Pat. No. 5,004,614, the opening(s) preferably comprise about 10-60% of the total face area of the tablet i.e. the upper and lower surfaces of a biconvex tablet. In the present invention, the opening(s) may comprise 0.25 to 70%, such as 10-70% of the total face area.

Alternatively, it may be useful to characterise the rate controlling effect of the opening(s) by reference to the area of the opening(s) relative to the total surface area of the coated tablet. Additionally, especially in cases where the core erodes by undercutting of the edges of the opening(s), the rate controlling effect may be related to the total circumference of the opening(s).

An unexpected finding is that two openings, for example one on each primary surface of a biconvex tablet, release an active agent from the core at a rate marginally greater than that of a single opening of the same overall area. However the variability of the release rate from the two openings is less than the variability of release rate from the corresponding single opening. Therefore, in the preferred embodiment of the invention, the coating of the core is provided with two, or more than two, apertures leading to the core. More preferably, the erodable coating surrounding the core is provided with two, or more than two, openings extending substantially completely through said coating but not penetrating said core and communicating from the environment of use to said core.

Where more than one opening is provided, the openings may be located on the same face of the oral dosage form, or on different faces. Suitably, the oral dosage form has two openings, one on each opposing face. Suitably, the oral dosage form is a tablet having two opposed primary surfaces, each surface having one opening through the coating.

As a protection for the core material, to prevent contamination via the opening(s) before dosing, it may be desirable to provide a conventional seal coating to either the core, or to the dosage form after formation of the opening(s). The seal coat may be a sub-coat or over-coat to the erodable coating.

By adjustment of the above variables and the surface area of the exposed core, the release rates in the different environmental conditions can be harmonised to obtain comparable release rates under different body environments, and so achieve more constant dosing to a patient.

Preferably the dissolution rates of the oral dosage forms of this invention are arranged, for example by routine adjustment of the erodable coating and dimensions of the opening(s), so that the rate of release is substantially uniform in the different pH environments experienced by the dosage form on administration. Dissolution rates may be assessed by in vitro testing in solutions of the appropriate pHs. For example, when comparing dissolution in the stomach and intestine, tests may be carried out initially at pH 1.5 with a transfer to pH 6.8 after 2 hours or 4 hours, as an assumed time for residence in the stomach before emptying into the intestines of a notional patient in respectively fasted and fed conditions.

The present invention further provides a method for the treatment and/or prophylaxis of disorders in a human or non-human mammal susceptible to treatment by a pharmaceutically acceptable weak base, which comprises administering an oral dosage form of this invention comprising a pharmaceutically acceptable weak base or a pharmaceutically acceptable salt or solvate thereof to a human or non-human mammal in need thereof.

In a preferred embodiment the present invention provides a method for the treatment and/or prophylaxis of diabetes mellitus, conditions associated with diabetes mellitus and certain complications thereof, which method comprises administering an oral dosage form of this invention comprising Compound A or a pharmaceutically acceptable salt or solvate thereof, to a human or non-human mammal in need thereof.

As used herein the term "pharmaceutically acceptable" embraces compounds, compositions and ingredients for both human and veterinary use. For example the term "pharmaceutically acceptable salt" embraces a veterinarily acceptable salt. In particular, suitable pharmaceutically acceptable salted forms of Compound A include those described in European Patent Number 0 306 228 and International Patent Application, Publication Number WO94/05659.

Suitable pharmaceutically acceptable solvates include hydrates.

No adverse toxicological effects are indicated in the above mentioned treatments.

All publications, including but not limited to patents and patent applications, cited in this specification are herein incorporated by reference as if each individual publication were specifically and individually indicated to be incorporated by reference herein as though fully set forth.

In the following Examples, tablet cores were formed by conventional means by mixing together the active ingredients with excipients and compressing to form the tablet core. These Examples are intended to be by way of illustration rather than limitation of the present invention, and Compound A is used simply as one example of a weak base suitable for use with the present invention.

EXAMPLE 1

A core was formed from the following formulation:

| | % w/w |
|---|---|
| Compound A (as maleate salt) | 7.1 |
| HPMC | 30.0 |
| Lactose | 60.9 |
| Colloidal silicon dioxide | 0.5 |
| Magnesium stearate | 1.5 | by compression to form 7 mm normal concave tablets of 150 mg.

The tablet cores were coated with a polymethacrylate resin soluble at pH 5.5 to a total weight of 160 mg.

An opening of diameter 3.0 mm was drilled through the coating in each of the two primary surfaces of the coated cores to expose the surface of the core.

EXAMPLE 2

A core was formed from the following formulation:

| | % w/w |
|---|---|
| Compound A (as maleate salt) | 7.1 |
| HPMC | 20.0 |
| Lactose | 70.9 |
| Colloidal silicon dioxide | 0.5 |
| Magnesium stearate | 1.5 | by compression to form 7 mm normal concave tablets of 150 mg.

The tablet cores were coated with a polymethacrylate resin soluble at pH 5.5 to a total weight of 160 mg.

An opening of diameter 3.5 mm was drilled through the coating in each of the two primary surfaces of the coated cores to expose the surface of the core.

Due to the larger openings and lower HPMC content, the dosage forms of Example 2 exhibited a faster release of Compound A at pH 1.5 and pH 6.8.

Dissolution Tests

FIG. 1 shows dissolution rates for the formulations of Examples 1 and 2 starting at pH 1.5 with a transfer to pH 6.8 after 4 hours, as an assumed time for residence in the fed stomach before emptying into the intestines. The medium for this dissolution test is initially an aqueous solution of sodium chloride and hydrochloric acid, pH 1.5 to mimic the pH found in the stomach environment. This medium is then titrated to pH 6.8 by the addition of aqueous sodium dodecyl sulfate and an aqueous solution of sodium acetate and tris(hydroxymethyl)methylamine after 4 hours to mimic the pH found in the intestine. FIG. 1 shows that with an erodable coat, the release is substantially complete i.e. over 90% release is achieved, after about 8 hours for the formulation of Example 2, and 12 hours for the formulation of Example 1. During that period, the rate of release is substantially uniform at both pHs, for both formulations.

Testing in the same solutions with transfer at 2 hours to mimic gastric emptying in the fasted condition, gave similar results.

The invention claimed is:

1. A tablet oral dosage form comprising:
    (i) an erodable core, which core comprises a pharmaceutically active weak base or a pharmaceutically acceptable salt or solvate thereof; and
    (ii) a pH-dependent erodable coating around said core, which coating has a thickness in the range 0.05 to 0.5 mm and comprises one or more openings, wherein said openings are circular, drilled openings extending substantially completely through said coating but not penetrating said core and communicating from the environment of use to said core and have a diameter in the range 0.5 mm to 8 mm, wherein said openings comprise about 10 to 70% of the total face area of the dosage form;

wherein release of the pharmaceutically active weak base or a pharmaceutically acceptable salt or solvate thereof from the dosage form occurs:

through the one or more openings by the erosion of said erodable core and through erosion of said erodable coating at pH>4.5, wherein said erodable coating dissolves at pH>4.5 to expose all of said core to erosion.

2. The oral dosage form according to claim 1, wherein the erodable coating is selected from a polymethacrylate polymer, coprocessed polyvinylacetate phthalate, cellulose acetate trimellitate, cellulose acetate phthalate, shellac, a hydroxyropyl-methylcellulose phthalate polymer and their copolymers, and blends thereof.

3. The oral dosage form according to claim 1, wherein the erodable coating comprises two drilled openings.

4. The oral dosage form according to claim 1, wherein the erodable core is in a multi-layered form.

5. The oral dosage form according to claim 1, wherein the core is predominantly comprised of hydroxypropylmethyl cellulose and lactose.

6. The oral dosage form according to claim 1, wherein the pharmaceutically acceptable weak base is selected from bupropion, ondansetron, paroxetine, valaciclovir, and 5-[4-[2-(N-methyl-N-(2-pyridyl)amino)ethoxy]benzyl]thiazolidine-2,4-dione, or a pharmaceutically acceptable salt or solvate thereof.

7. An oral dosage form according to claim 1, in which the pharmaceutically acceptable weak base is 5-[4-[2-(N-methyl-N-(2-pyridyl)amino)ethoxy]benzyl]thiazolidine-2,4-dione or a pharmaceutically acceptable salt or solvate thereof.

8. A process for the preparation of an oral dosage form according to claim 1, which process comprises:
(a) preparing an erodable tablet core;
(b) coating the core with a material with pH-dependent erodability; and
(c) creating one or more openings in the coating, wherein said one or more openings extend substantially completely through said coating but not penetrating said core and communicating from the environment of use to said core.

* * * * *